United States Patent
Kantsevoy et al.

(10) Patent No.: US 7,959,640 B2
(45) Date of Patent: Jun. 14, 2011

(54) METHOD OF PERFORMING TRANSGASTRIC VENTRAL HERNIA REPAIR AND TISSUE ANCHORS AND DEPLOYMENT DEVICES THEREFOR

(75) Inventors: Sergey Veniaminovich Kantsevoy, Owings Mills, MD (US); Vladimir Mitelberg, Austin, TX (US); Donald K. Jones, Dripping Springs, TX (US)

(73) Assignee: Apollo Endosurgery, Inc., Austin, TX (US)

( * ) Notice: Subject to any disclaimer, the term of this patent is extended or adjusted under 35 U.S.C. 154(b) by 508 days.

(21) Appl. No.: 12/030,244

(22) Filed: Feb. 13, 2008

(65) Prior Publication Data

US 2009/0204130 A1 Aug. 13, 2009

(51) Int. Cl.
*A61B 17/08* (2006.01)
(52) U.S. Cl. ........................................ 606/151
(58) Field of Classification Search .......... 606/151, 606/153, 154, 300, 301; 128/898; 411/378, 411/383, 411
See application file for complete search history.

(56) References Cited

U.S. PATENT DOCUMENTS

| | | | | |
|---|---|---|---|---|
| 2,391,792 A * | 12/1945 | Miles et al. | 52/513 |
| 4,762,453 A * | 8/1988 | DeCaro | 411/383 |
| 4,917,554 A * | 4/1990 | Bronn | 411/392 |
| 5,728,116 A * | 3/1998 | Rosenman | 606/151 |
| 5,810,882 A * | 9/1998 | Bolduc et al. | 606/213 |
| 5,904,696 A * | 5/1999 | Rosenman | 606/151 |
| 6,132,438 A * | 10/2000 | Fleischman et al. | 606/139 |
| 6,258,119 B1 * | 7/2001 | Hussein et al. | 623/1.22 |
| 6,276,883 B1 * | 8/2001 | Unsworth et al. | 411/324 |
| 6,423,062 B2 * | 7/2002 | Enayati | 606/59 |
| 6,613,059 B2 | 9/2003 | Schaller et al. | |
| 6,663,633 B1 * | 12/2003 | Pierson, III | 606/148 |
| 6,960,217 B2 * | 11/2005 | Bolduc | 606/108 |
| 6,960,221 B2 | 11/2005 | Ho et al. | |
| 6,964,652 B2 * | 11/2005 | Guiles et al. | 604/117 |
| 7,776,057 B2 * | 8/2010 | Laufer et al. | 606/139 |
| 2001/0049497 A1 | 12/2001 | Kaloo et al. | |
| 2002/0055742 A1 * | 5/2002 | Lieberman | 606/73 |
| 2002/0087170 A1 * | 7/2002 | Kuhns et al. | 606/143 |
| 2003/0167071 A1 * | 9/2003 | Martin et al. | 606/232 |
| 2003/0208211 A1 * | 11/2003 | Kortenbach | 606/151 |
| 2004/0092937 A1 * | 5/2004 | Criscuolo et al. | 606/72 |
| 2004/0092970 A1 * | 5/2004 | Xavier | 606/151 |
| 2004/0127916 A1 * | 7/2004 | Bolduc et al. | 606/151 |
| 2004/0254572 A1 * | 12/2004 | McIntyre et al. | 606/41 |
| 2005/0273138 A1 | 12/2005 | To et al. | |
| 2005/0277942 A1 * | 12/2005 | Kullas et al. | 606/99 |
| 2005/0288691 A1 * | 12/2005 | Leiboff | 606/151 |
| 2006/0129154 A1 * | 6/2006 | Shipp | 606/73 |
| 2007/0043255 A1 * | 2/2007 | O'Donnell | 600/30 |
| 2007/0055206 A1 | 3/2007 | To et al. | |
| 2009/0018592 A1 * | 1/2009 | Pitbladdo | 606/309 |

\* cited by examiner

*Primary Examiner* — Darwin P Erezo
*Assistant Examiner* — Son Dang
(74) *Attorney, Agent, or Firm* — Gordon & Jacobson, PC

(57) ABSTRACT

A translumenal approach through a natural body cavity to repair a ventral hernia is provided. In a transgastric approach, the abdominal cavity is accessed via an incision through a wall of the digestive tract. A system for the deployment of tissue anchors to anchor a tissue reinforcing mesh to repair the ventral hernia is provided. Particular tissue anchors are disclosed. In certain embodiments, the tissue anchors include a shaft and a head reconfigurably coupled to the shaft permitting the head and shaft to be in a substantially parallel loaded configuration and in a substantially transverse deployed configuration. In addition, tissue anchors may include biodegradable and non-biodegradable components, with the non-biodegradable component defining spaces for soft tissue ingrowth upon degradation of the biodegradable component.

9 Claims, 6 Drawing Sheets

METHOD OF PERFORMING TRANSGASTRIC VENTRAL HERNIA REPAIR AND TISSUE ANCHORS AND DEPLOYMENT DEVICES THEREFOR

BACKGROUND OF THE INVENTION

1. Field of the Invention

This invention relates broadly to surgery. More particularly, this invention relates to methods of performing minimally invasive surgical procedures, tissue anchors, and tissue anchor deployment devices.

2. State of the Art

Hernia is a general term used to describe a bulge or protrusion of an organ through the structure or muscle that usually contains. One type of hernia is a ventral hernia, and occurs in the midline of the abdominal wall, usually above the navel (umbilicus). A ventral hernia may be congenital but is most often acquired as a result of a prior surgical incision. In fact, incisional hernias are reported to occur in approximately 4% to 10% of patients after open surgical procedures. Certain risk factors predispose patients to develop incisional ventral hernias, including obesity, diabetes, respiratory insufficiency (lung disease), steroids, wound contamination, postoperative wound infection, smoking, inherited disorders such as Marfan's syndrome and Ehlers-Danlos syndrome, as well as poor surgical technique. A ventral hernia must be surgically repaired. Approximately 90,000-100,000 ventral hernia repairs are performed annually in the United States.

Throughout most of the history of surgery and often today, ventral hernia repair was and is performed by another open procedure. That is, the abdomen is surgically incised over the area of the hernia, with the incision carried down carefully through the sequential tissue layers. The goal is to separate away all the normal tissue and define the margins of the hole or weakness. Once this has been achieved, the hole is then closed, usually by some combination of suture and a plastic mesh. When a repair is done by suture alone, the edges of the defect are pulled together, much like sewing a hole together in a piece of cloth. One of the problems with this approach is that it can put excessive strain on the surrounding tissues through which the sutures are passed. Over time, with normal bodily exertion, this strain can lead to the tearing of these stressed tissues and the formation of another hernia.

In order to provide a secure repair and avoid the stress on the adjacent tissue caused by pulling the hole closed, the hole or weakness is often bridged with a piece of plastic-like mesh or screen material. The mesh is a permanent material and, when sewn to the margins of the defect, it allows the body's normal healing process to incorporate it into the local structures.

While this repair is effective, the trauma to the patient from the procedure can present significant issues for the patient, including extended recovery time. Moreover, there is the danger of complication as prolonged exposure of surgical wounds to the open environment heightens the chance of infections even in presumably sterile settings.

In the last decade or so, a minimally invasive surgical approach to ventral hernia repair has become possible and more commonly used. In this approach, several laparoscopic instruments are introduced through small incisions into the abdomen. The instruments include a visualization scope, a pressurization pathway to insufflate the abdomen, and two or more manipulating instruments (e.g., grasping forceps, staplers, tackers, suturing devices, etc.). The instruments are manipulated to introduce and place the mesh under the hernia defect with a wide margin of mesh outside the defect. The mesh is anchored into place with suture and/or secured to the anterior abdominal wall with a varying number of tacks, placed laparoscopically. The mesh minimizes tension on the repair. The instruments are removed and the several wounds extending into the abdominal cavity are closed.

Minimally invasive surgery results in less operative trauma for the patient. It is also less expensive, reduces hospitalization time, causes less pain and scarring, and reduces the incidence of complications related to the surgical trauma, speeding the recovery. However, even in minimally invasive procedures through the abdomen, wounds are made in the body that are of such significant dimension that they need to be stapled or sutured closed after instrument removal. Such wounds are subject to pain and discomfort, and are a site for adhesions.

SUMMARY OF THE INVENTION

In accord with one aspect of the invention a minimally invasive method of performing surgical repair of a ventral hernia is provided which is less invasive than currently performed minimally invasive methods. Such method of the invention includes a transgastric or translumenal approach through a natural body cavity to position a mesh material over the hernia. In one embodiment, via a transgastric approach, the abdominal cavity is accessed via an incision through a wall of the digestive tract. An overtube with a conduit is inserted and anchored within the incision, and an endoscope and one or more surgical instruments required for the surgical repair are inserted through the overtube. A grasper is preferably used to deliver the mesh through the overtube or a working channel of the endoscope in a folded configuration. The graspers are used to position the mesh to the abdominal wall adjacent the hernia. A tissue anchor deployment device is used to deploy tissue anchors through a portion of the mesh material near the graspers to attach the mesh to the abdominal wall. The mesh can be alternatively preloaded onto an anchor provided in the deployment device to facilitate initial tacking of the mesh to the wall. The graspers then position another portion of the mesh across the hernia where the deployment device is used to deploy another anchor to attach the mesh to the wall. The process is continued until the mesh material sufficiently bridges the hernia and is secured in place. The graspers, deployment device and endoscope are then removed from the abdominal cavity, followed by the overtube, and the access incision is closed. The graspers and deployment device can be provided in a co-axial arrangement, and even integrated into a single instrument.

In accord with another aspect of the invention, various tissue anchors for use with the tissue anchor deployment device are provided to anchor the tissue reinforcing mesh. Embodiments of tissue anchors includes a shaft and a head reconfigurably coupled to the shaft permitting the head and shaft to be in a substantially parallel loaded configuration and in a substantially transverse deployed configuration. Such reconfigurable coupling of the head and shaft can be, e.g., as a result of a resilient live hinge, a mechanical pivot, or a shape memory activatable region. In one embodiment, the shaft includes a distal barb, and when the head and shaft are in the loaded configuration, the barb leads the head. In use, the barb of the shaft is introduced through the mesh and into the abdominal wall and the anchor is then reconfigured into the deployed configuration such that the head and barb are located on opposite sides of the mesh to retain the mesh to the wall. In another embodiment, the head leads the shaft, the head is introduced through the mesh and into the tissue and then reconfigured into a transverse relationship relative to the shaft. The shaft may include a proximal eye and a slidable cinch which is tightened against the mesh to deploy the anchor into the reconfigured shape. Suture can be strung through the eyes of several such anchors to individually secure the anchors to the mesh and abdominal wall and/or the anchors to each other.

In accord with other aspects of the anchors, sharp and/or piercing portions of the anchor can be comprised of a biodegradable material, while other portions are non-biodegradable. After biodegradation, the sharp/piercing portions are eliminated for safer long term implantation. In addition, after biodegradation, the remaining structure may include a geometry that facilitates tissue in-growth to further secure the anchor within the tissue.

DETAILED DESCRIPTION OF THE PREFERRED EMBODIMENTS

Figure 1:
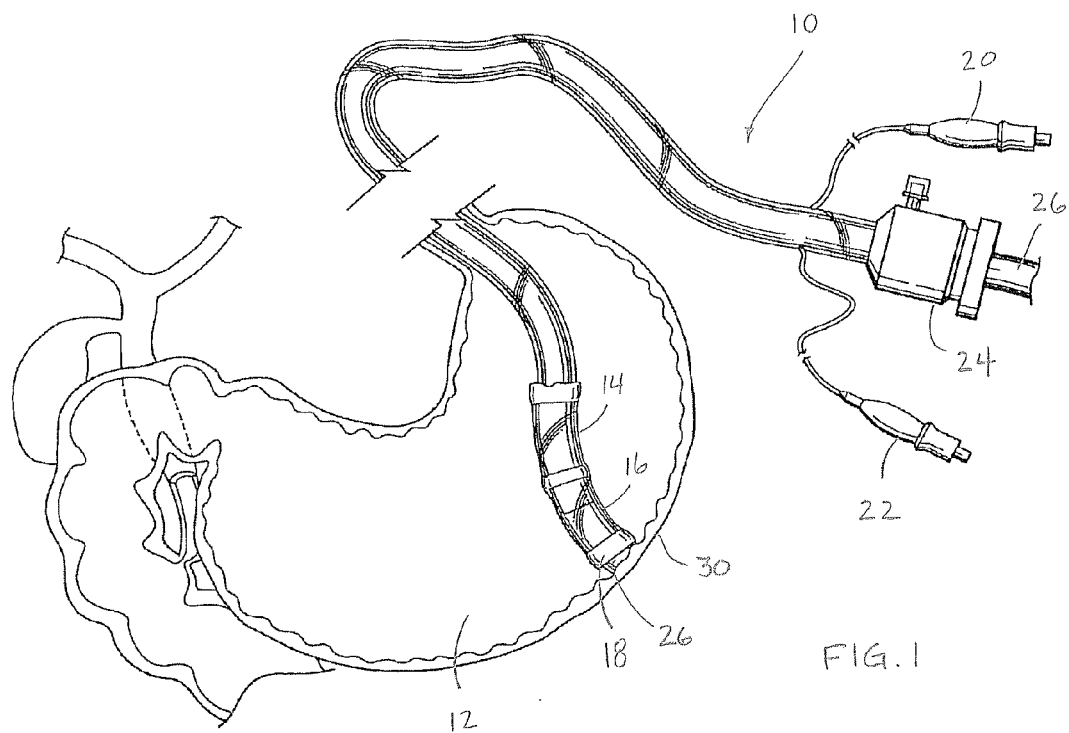
FIG. 1 illustrates an overtube with a endoscope inserted transgrastically, with balloons of the overtube in a deflated state.
Figure 2:
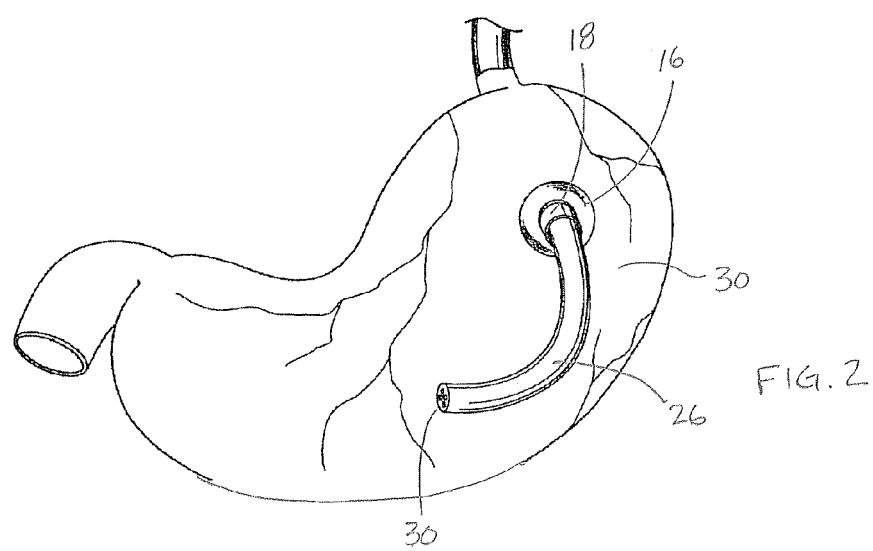
FIG. 2 illustrates the overtube of FIG. 1 inserted through the gastric wall with balloons inflated on both sides of the gastric wall and an endoscope extending through the overtube.
Figure 3:
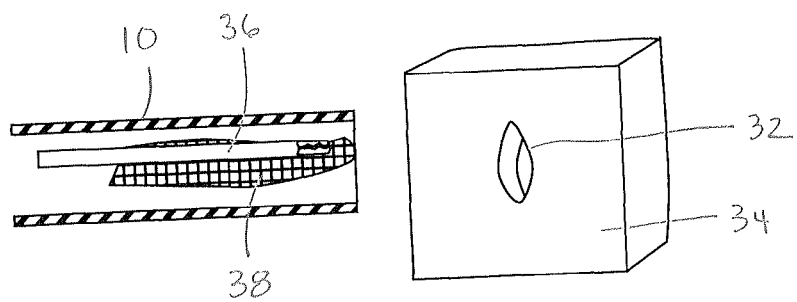
FIG. 3 is a schematic illustration of an instrument inserted through the overtube delivering a mesh to a ventral hernia site.

A method and device for performing a transgastric ventral hernia repair on a human according to the invention is provided. Referring to FIG. 1, in carrying out the method, a natural orifice transgastric endoscopic surgery (NOTES) access kit is preferably used to access the peritoneal cavity. One embodiment of a NOTES access kit includes an overtube device 10, which is inserted transgastrically into the stomach 12. The overtube device 10 includes distal and proximal balloons 14, 16 adjacent its distal end 18. The balloons 14, 16 are inflatable via respective actuators 20, 22 at a proximal end 24 of the overtube device 10. A steerable endoscope 26 is positioned within the overtube and an endoknife (needle knife), not shown, is passed through a working channel 28 (FIG. 2) of the endoscope and used to incise an opening in the stomach wall 30 under visualization of the endoscope. Referring to FIG. 2, the distal end 18 of the overtube device is then passed through the incision until the distal balloon 16 is located outside the stomach wall 30 and within the peritoneal space. The actuators 20, 22 are then operated to inflate the balloons 14, 16 to lock the distal end 18 of the overtube relative to the stomach wall and form a preferably fluid tight seal with the wall 30 of the stomach 12. An overtube device 10 and the use thereof are described in more detail in U.S. Pub. No. 2001/0049497A1, which is hereby incorporated by reference herein in its entirety.

The peritoneal cavity may be insufflated to facilitate visualization of the peritoneal tissue and particularly the ventral hernia, and also to facilitate instrument movement and safety to the patient. Insufflation may be accomplished with a small diameter insufflation port inserted through the overtube device 10 or punctured through the abdomen in a location spaced apart from the hernia and the locus of the intended repair.

Figure 4:
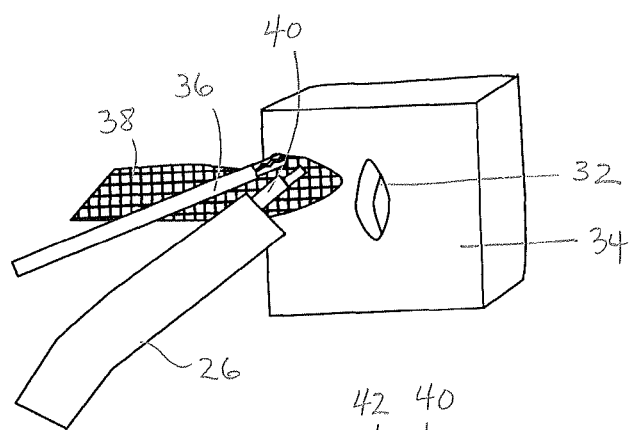
FIGS. 4-6 are schematic illustrations of an anchor delivery device inserted through an endoscope within the overtube cooperating with the grasper to anchor the mesh relative to the hernia.
Figure 5:
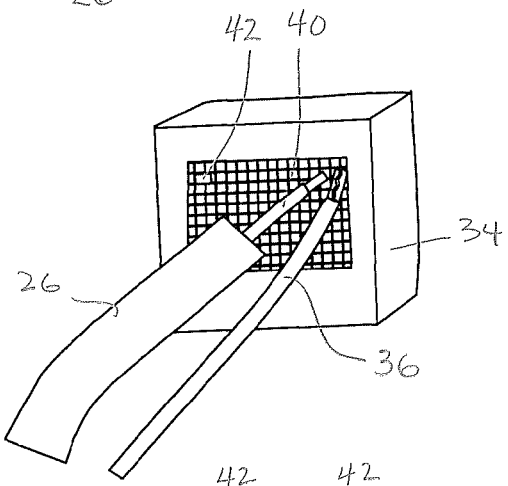
Figure 6:
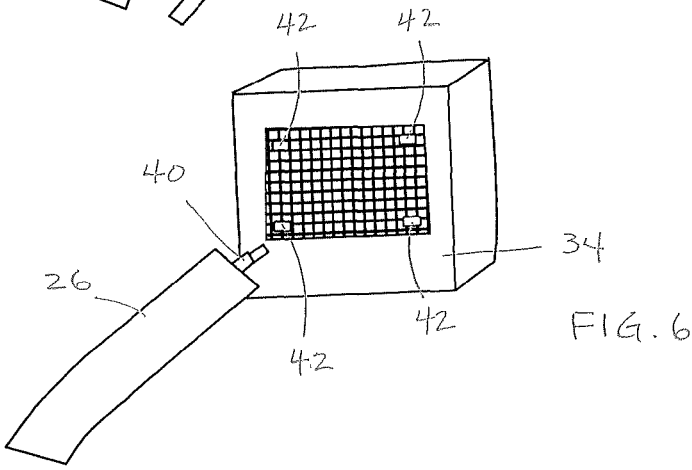

Referring to FIG. 5, a grasping instrument, e.g., forceps 36 is provided with a mesh material 38 in a folded configuration and then also inserted through the overtube 10 (or a working channel of the endoscope 26) to deliver and position the mesh material 38 to the abdominal wall 34 adjacent the hernia 32. The endoscope 26 is preferably steered toward the ventral hernia 32 and, as shown in FIGS. 4 through 6, a tissue anchor deployment device 40 is then used to deploy tissue anchors 100 (generally, but any of the variations described below can be used), to pierce a portion of the mesh material 38 about a perimeter thereof near the forceps 36 to attach the mesh material 38 to the abdominal wall 34. The mesh material 38 can be alternatively preloaded onto the initial anchor deployed by the tissue deployment device 40 to facilitate initial tacking of the mesh material 38 to the abdominal wall. The forceps 36 is then used to position another perimeter portion of the mesh material 38 about the hernia 32, and the anchor deployment device 40 is used to deploy another anchor 100 to attach the mesh material to the wall.

Figure 7:
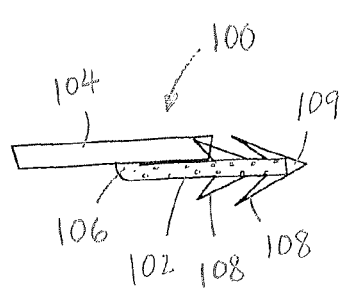
FIGS. 7 and 8 are schematic illustrations of a first embodiment of an anchor according to the invention, in a loaded configuration and a deployed configuration within tissue.
Figure 8:
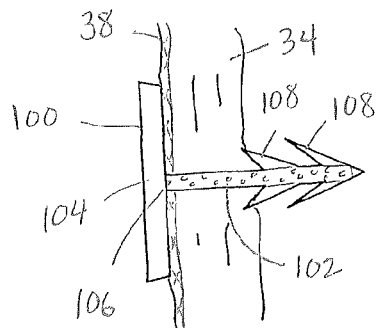

Various tissue anchors can be used with the tissue anchor deployment device to anchor the mesh material 38 to repair the ventral hernia. Referring to FIGS. 7 and 8, a first embodiment of a tissue anchor 100 includes a shaft 102 and a head 104 reconfigurably coupled to the shaft permitting the head and shaft to be in a substantially parallel loaded configuration (FIG. 7) when loaded within the deployment device 40 (FIGS. 4-6), and a deployed configuration (FIG. 8) in which the shaft and head are oblique to each and preferably in T-shaped configuration. Such reconfigurable coupling of the shaft 102 and head 104 can be, e.g., as a result of a resilient live hinge 106, a shape memory heat activatable region, or a rotatable pivot. The shaft 102 includes two distal barbs 108 and a pointed tip 109, and when the head and shaft are in the loaded configuration, the barbs 108 and tip 109 lead the head 104. In the deployed configuration, the head 104 is rotated on the hinge 106 relative to the shaft 102. The barbs 108 retain the anchor 100 within the abdominal wall 34, while the head 104 retains the mesh material 38 against the abdominal wall.

Figure 9:
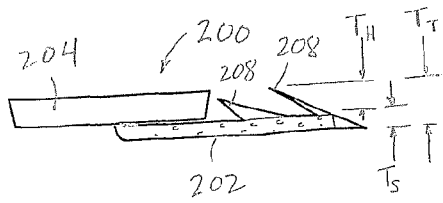
FIGS. 9 and 10 are schematic illustrations of a second embodiment of an anchor according to the invention, in a loaded configuration and a deployed configuration within tissue.
Figure 10:
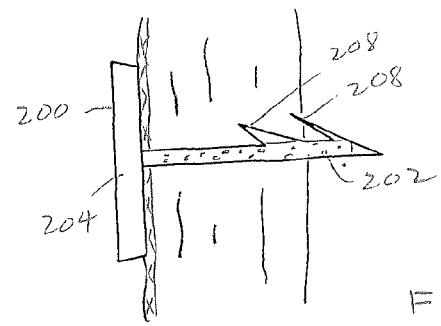

Referring to FIGS. 9 and 10, a second embodiment of a tissue anchor 200 is shown in both loaded and deployed configurations. Anchor 200 is substantially similar to anchor 100, but includes barb portions 208 extending on only one side of shaft 202 to reduce the profile or diameter of the anchor for placement with anchor deployment device. To facilitate delivery of the anchor 200, the barb portions 208 can be eliminated from the side of the shaft opposite the head 204 (when in the loaded configuration) and in a direction opposite thereof the barb portions 208 do not extend beyond the head 204, such that in the loaded configuration the barb portions are constrained to the thickness $T_H$ of the head and the entire anchor has a total thickness $T_T$ of approximately $T_H$+diameter of the shaft ($T_S$).

Figure 11:
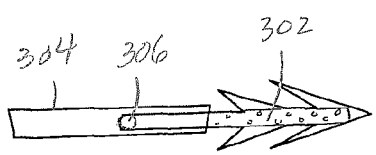
FIGS. 11 and 12 are schematic illustrations of a third embodiment of an anchor according to the invention, in a loaded configuration and a deployed configuration within tissue.
Figure 12:
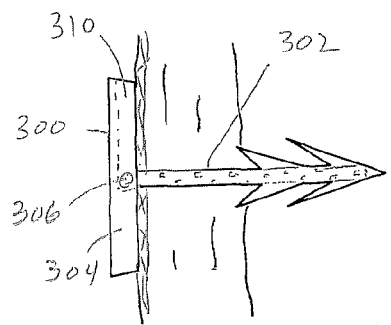

Referring to FIGS. 11 and 12, a third embodiment of a tissue anchor 300, substantially similar to tissue anchor 100, is shown in both loaded and deployed configurations. Tissue anchor 300 is shown specifically with a mechanical pivot 306 permitting rotation of the head 304 relative to the shaft 302. Thus, the shaft 302 and head 304 are preferably in alignment with both head and shaft extending through a common plane (by way of the shaft extending through a slot 310 in the head) when in the loaded configuration. This configuration also minimizes $T_T$ of the anchor.

Figure 13:
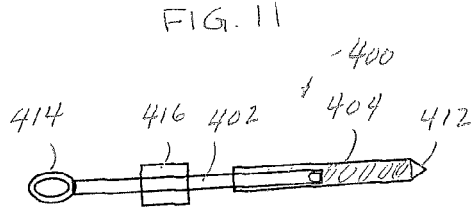
FIGS. 13 and 14 are schematic illustrations of a fourth embodiment of an anchor according to the invention, in a loaded configuration and a deployed configuration within tissue.
Figure 14:
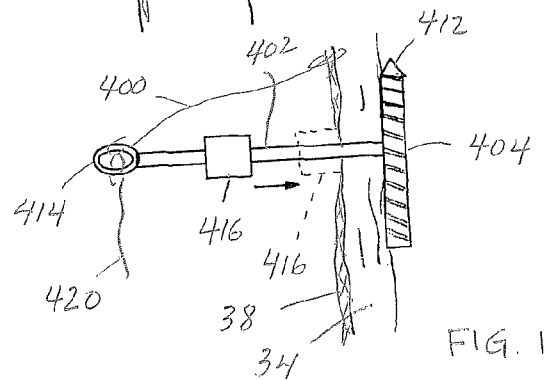

Referring to FIGS. 13 and 14, a fourth embodiment of a tissue anchor 400 is shown. Tissue anchor 400 includes a shaft 402 and a head 404, the shaft and head reconfigurable between a loaded configuration, in which the head 404 leads the shaft 402, and a deployed configuration, in which the shaft moves transversely relative to the head. The head 404 includes at least one sharpened end 412 which is adapted to be introduced through the mesh 38 and into the tissue 34. The shaft 402 may include a proximal eye 414 and a slidable cinch 416 which can be tightened against the mesh 38. The cinch 416 may ratchet over structure on the shaft 402 to permit one-way movement thereover. The cinch may facilitate deployment of the anchor 400 into the reconfigured shape and/or hold the mesh 38 tightly against the tissue 34. Suture 420 can be strung through the eye 414 to individually secure the anchor to the mesh material 38 and abdominal wall 34 and through several eyes to secure the anchors 400 to each other.

Figure 19:
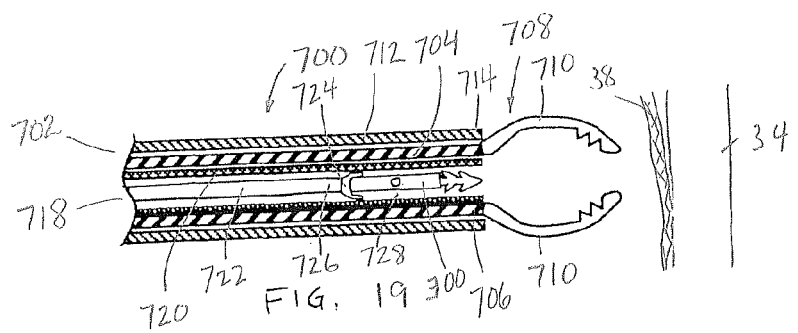
FIGS. 19-23 illustrate the implantation of a tissue anchor through a mesh material and into the abdominal wall.

The tissue anchors are sized for loading within a tissue chamber 728 of the anchor deployment device 40, described below (FIG. 19). The tissue chamber 728 has a diameter not exceeding approximately 3 mm, and generally smaller, e.g., approximately 2 mm. Thus, the diameter or cross-wise dimension of the head portions of the respective tissue anchors should not exceed 3 mm, and should be preferably approximately 2 mm.

All embodiments of the anchors can be made of biocompatible metals including stainless steel, titanium alloys, nickel-titanium shape memory alloy, biocompatible plastics, shape memory plastics, or a composite of both substantially inert and biodegradable materials.

Figure 15:
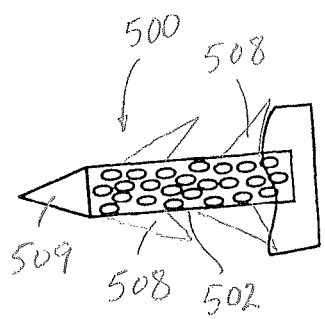
FIG. 15 is a schematic illustration of a tissue anchor including one embodiment of permanent and biodegradable portions.
Figure 16:
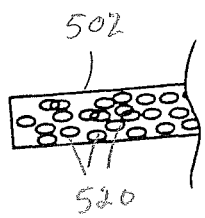
FIG. 16 is a schematic illustration of the tissue anchor of FIG. 15, without the biodegradable portion.
Figure 17:
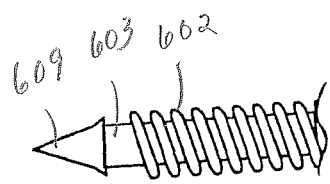
FIG. 17 is a schematic illustration of a tissue anchor including another embodiment of permanent and biodegradable portions.

More particularly, referring to FIG. 15, sharp and/or piercing portions 508, 509 of the anchor can be comprised of one or more biodegradable material, while other portions of the anchor 500 are made from one or more non-biodegradable materials. Referring to FIG. 16, after biodegradation of the biodegradable material, the sharp/piercing portions are eliminated from the shaft 502 for safer long term implantation. In addition, after biodegradation, the remaining shaft structure may include a geometry that facilitates tissue in-growth to further secure the anchor within the tissue. By way of example, the shaft 502 may define a tubular structure with interstices 520 dimensioned for tissue ingrowth. Referring to FIG. 17, another example of an anchor structure is shown.

Figure 18:
FIG. 18 is a schematic illustration of the tissue anchor of FIG. 17, without the biodegradable portion.

Upon implantation, the anchor includes a non-biodegradable coil shaft 602, and a biodegradable internal post 603 with piercing tip 609. Referring to FIG. 18, after implantation and upon biodegradation of the post 603, spaces 611 are provided between the coils for tissue ingrowth.

Turning now to FIG. 19, one embodiment of a system 700 for attaching the mesh material 38 to the abdominal wall 34 is shown. The system 700 includes a grasping forceps 36 and anchor deployment device 40 in coaxial arrangement (although it is understood that they may be used separately in a non-coaxial arrangement as shown in FIGS. 4 and 5). The grasping forceps 36 and deployment device 40 can be discrete instruments with separate proximal handles (not shown), or can be integrated into a single instrument with a common proximal handle (not shown). It is, of course, understood that the forceps 36 and deployment device 40 of the system 700 have sufficient length and are sufficiently flexible (i.e., are capable of being flexed through a tortuous path preferably of at least 360°), to enable the intended procedure.

Figure 20:
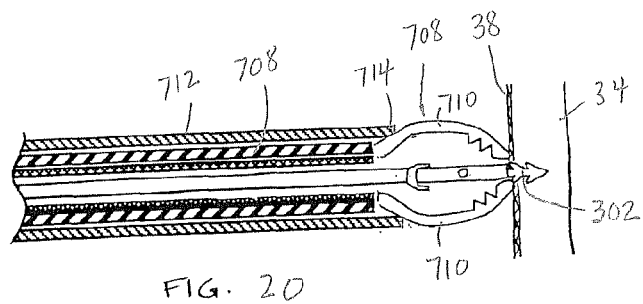

The grasping forceps 36 includes a first tubular member 704 including a distal end 706 provided with an end effector assembly 708 including, e.g., a pair of forceps jaws 710. A sleeve 712 is provided over the first tubular member 704 and is reciprocal thereto such that a distal end 714 of the sleeve can be forced over a portion of the end effector assembly 708 to effect closure and even clamping of the jaws 710 (FIG. 20). Proximal movement of the distal end 714 of the sleeve 712 relative to the end effector assembly 708 then effects release of the jaws 710 into an open position. Alternatively, other means including, e.g., control wires, can be used to effect operation of the jaws 710.

The deployment device 40 of the extends coaxially through the first tubular member 704 of the grasping forceps 36 and is longitudinally displaceable therein. The deployment device 40 includes a second tubular member 720 and a control member 722 longitudinally movable within the tubular member 720. A pusher 724 or other anchor engagement structure is provided at the distal end 726 of the control member 722. An anchor, e.g., anchor 300 (or any anchor described herein or any other suitable anchor) is loaded in a chamber 728 at the distal end of the second tubular member 720 and engaged by the pusher 724. It is appreciated that the few components and compact design of the deployment device 40 make it suitable for working through the lumen defined by the first tubular member of the grasping forceps, or working directly through the working channel of an endoscope. The deployment device preferably has an outer diameter of approximately 2 to 3 mm.

Referring to FIGS. 2 and 19, in use, the system 700, with anchor 300 loaded therein, is advanced through the overtube device 10 and preferably through a working channel 28 of the endoscope 26 toward the abdominal wall 34 at the site of the ventral hernia. The grasping forceps may be initially provided with the mesh material 38 or the mesh material may be delivered to the site with another instrument and held against the wall. The sleeve 712 of the grasping forceps 36 is moved relative to the first tubular member 704 to grip and fix the mesh material 38 at the location of intended anchor deployment.

Figure 21:
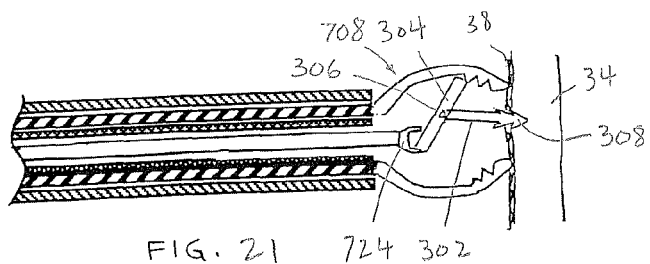

Turning to FIG. 20, the control member 722 of the deployment device 40 is moved relative to the second tubular member 720 to advance the pusher 724 and force a distal portion of the anchor 300 (e.g., shaft 302) through the mesh material 38 and into the abdominal wall 34. Referring to FIG. 21, the anchor 300 is then reconfigured into the deployed configuration such that the head 304 and barbs 308 on the shaft 302 are located on opposite sides of the mesh material 38, with the barbs within or through a portion of the abdominal wall 34 to retain the mesh material 38 to the wall 34. The head 304 of the anchor 300 can be reconfigured about the hinge 306 into the deployed configuration by manipulation with the end effector assembly 708 of the grasping forceps 36 and the pusher 724 of the deployment device 40. Alternatively, when the hinge of the anchor is resilient, the head may automatically spring into the deployment configuration once it leaves the deployment device 40. In yet another alternative, when the hinge is constructed from a shape memory alloy or polymer, the pusher can be coupled to an electromagnetic heat source to apply heat to the anchor to effect transformation into the reconfigured shape. As yet another alternative with respect to a shape memory alloy shape memory polymeric anchor, a discrete heat application instrument may be used to apply focused or dispersed heat to the area of the anchor to effect transformation into the reconfigured shape.

Figure 22:
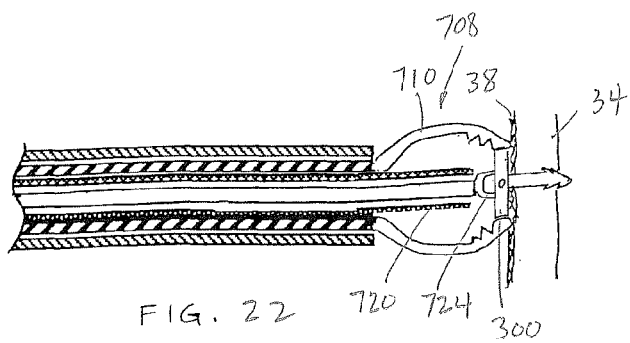
Figure 23:
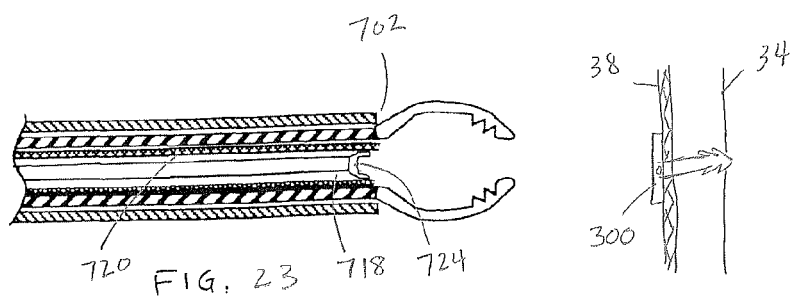

Turning to FIG. 22, after the anchor 300 is reconfigured, it is fully seated against the mesh material 38, with the shaft extending as far as possible within the abdominal wall 34. Such seating can be effected by application of force from the pusher 724 of the deployment device, from one or both jaws 710 of the end effector assembly 708 of the grasping forceps, or from a portion of a separate and discrete additional instrument. If the pusher 724 is used to apply force, the second tubular member 720 is preferably advanced with the pusher to increase the stability of the control member 722 and pusher 724. Referring to FIG. 23, once the anchor 300 is seated, the pusher 724 is withdrawn into the second tubular member 720, and the deployment device 40 is withdrawn into the grasping forceps 36. Where the deployment device stores only a single anchor, the deployment device is withdrawn entirely from the grasping forceps, out of the patient, reloaded with another anchor and then re-inserted co-axially relative to the grasping forceps. Alternatively, a separate single-use instrument may be used for each anchor that is deployed. Furthermore, a multi-anchor deployment device that can deploy multiple anchors in sequence without removal from the patient can be used.

The deployment device 40 and grasping forceps 36 are then relocated to another area of the mesh material 38 for application of another anchor. The process is continued until the mesh material 38 is sufficiently anchored to surgically support the ventral hernia.

Figure 24:
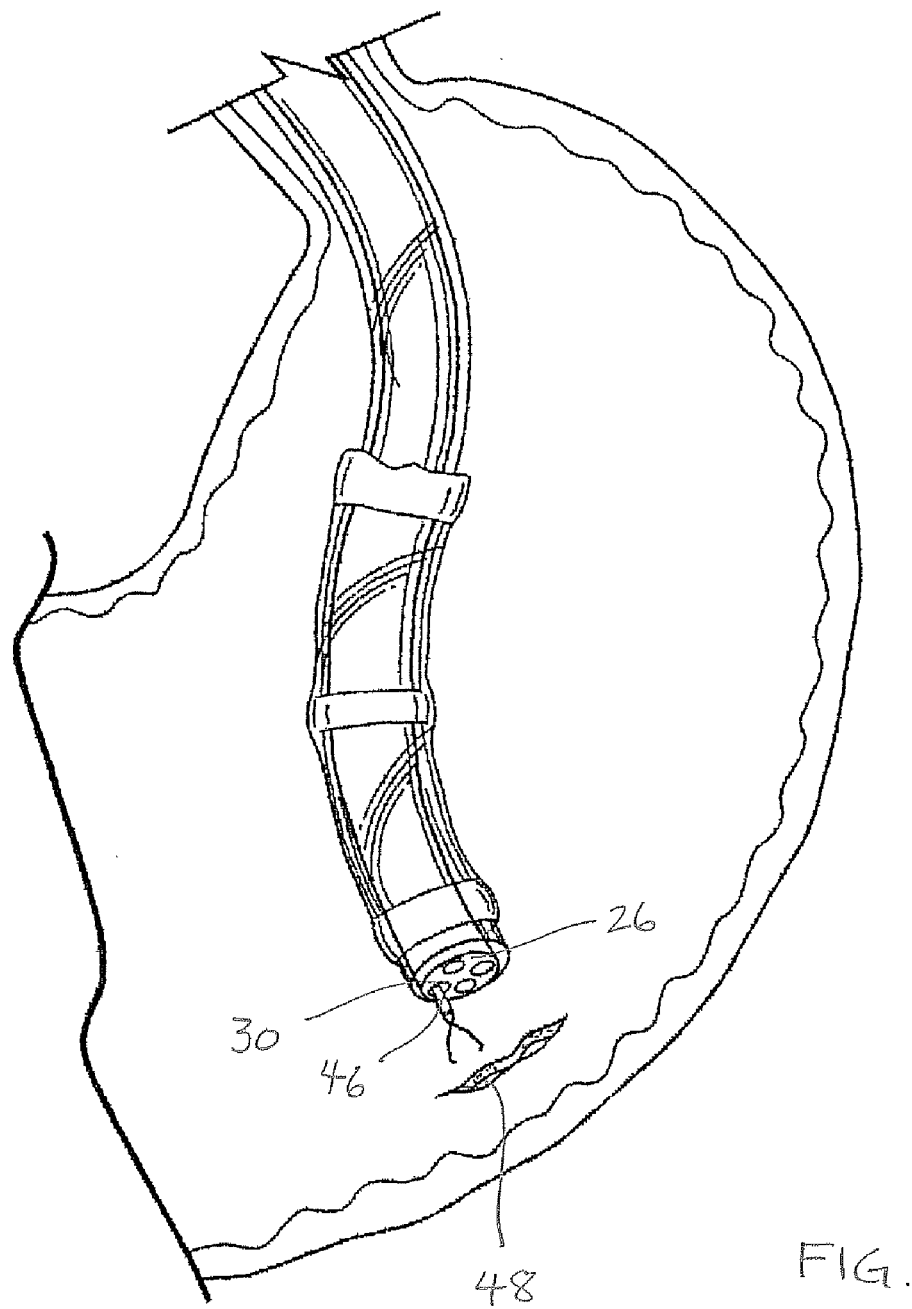
FIG. 24 illustrates an incision in the stomach wall being closed by an endoscopic clip applier.

Once the mesh material is secured in place, the grasping instrument 36, the anchoring deployment device 40 and the endoscope 26 may be removed from the abdominal cavity, and withdrawn into the overtube device 10. The balloons 14, 16 of the overtube device 10 are then deflated via operation of the actuators 20, 22 and the distal end 18 of the overtube device 10 is retracted into the stomach 12. Referring to FIG. 24, a closure instrument such as a clip applier 46, stapler, ligator, or suturing device, is then inserted into the stomach 12, preferably through a working channel 30 of the endoscope 26 or outside the endoscope and through the overtube device, and operated to close the incision 48 in the stomach wall 30.

The advantages of the above described procedure include minimizing the trauma of access to internal organs and decreasing the time of the surgical procedure. By avoiding an incision through the muscular abdominal wall, many post-operative problems are eliminated. Furthermore, the patient is provided with reduced anesthetic as the procedure is shortened and the trauma is decreased. The need for strong post-operative pain medications is drastically reduced so that the drowsiness, fatigue and unsteadiness they cause are virtually eliminated, and it is possible to return to normal activities in a fraction of the time necessary after regular surgery.

It is anticipated that further reducing trauma to the body during surgical procedures and reducing the time of a surgical procedure will provide better surgical outcomes and decreased recovery times.

There have been described and illustrated herein several embodiments of methods for performing transgastric repair of a ventral hernia, anchors therefor, and instruments for the use therewith. While particular embodiments of the invention have been described, it is not intended that the invention be limited thereto, as it is intended that the invention be as broad in scope as the art will allow and that the specification be read likewise. Thus, while a particular order to the insertion of various instruments has been disclosed, it will be appreciated that the instruments may be inserted in an order other than as described. Moreover, while the preferred approach is transgastric, another approach through a different natural body orifice, such as through the anus and intestines, can be used. In addition, while particular anchors have been described as well as instruments for their deployment, it will be understood that other anchors and deployment devices can be used as well. Moreover, the anchors and system for deployment thereof may be used for other surgical procedures. Further, all uses of the terms 'substantially' and 'approximately' indicate a potential variation in stated dimension of up to ±25 percent. Also, while certain preferred tissue anchors have been described, it is understood that other tissue anchors can be used in conjunction with the method and devices described herein (or a device modified for use therewith). By way of example, the tissue anchors described in U.S. Pub. Nos. 2005/0273138A1 and 2007/0055206A1, which are hereby incorporated by reference herein, are within the scope of anchors of the type which can be used in the present method, system, and can be modified in accord with the teachings herein. It will therefore be appreciated by those skilled in the art that yet other modifications could be made to the provided invention without deviating from its spirit and scope as claimed.

What is claimed is:

1. A method of performing a transgastric ventral hernia repair on a patient, comprising:
   a) extending a conduit translumenally into a gastric cavity of the patient;
   b) translumenally creating an incision through a wall of the gastric cavity;
   c) anchoring the conduit within the incision;
   d) inserting an endoscope through the conduit into a peritoneal space adjacent the ventral hernia;
   e) inserting a mesh material translumenally through the conduit to the ventral hernia;
   f) inserting a tissue anchor deployment device loaded with a tissue anchor through the conduit to the hernia, said tissue anchor including a coil and a post extending within the coil, said post made from a bioabsorbable material;
   g) deploying the tissue anchor to couple the mesh material relative to the ventral hernia;
   h) removing the conduit from the incision; and
   i) translumenally closing the incision in the wall of the gastric cavity.

2. A method according to claim 1, further comprising:
transgastrically inserting a grasping instrument through the conduit and to the ventral hernia; and
manipulating the mesh material with the grasping instrument.

3. A method according to claim 2, wherein:
the deployment device is inserted coaxially with the grasping instrument.

4. A method according to claim 2, wherein:
the deployment device is inserted through a working channel of the endoscope.

5. A method according to claim 1, wherein:
the deployment device has a diameter not exceeding approximately 3 mm.

6. A method according to claim 1, wherein:
the mesh material is inserted in a folded configuration.

7. A method according to claim 1, wherein:
the tissue anchor loaded within the deployment device includes biodegradable and non-biodegradable components.

8. A method according to claim 1, wherein:
the tissue anchor comprises a shape memory alloy.

9. A method according to claim 1, wherein:
the tissue anchor comprises nickel-titanium alloy.

* * * * *